US010610690B2

(12) United States Patent
Nabutovsky et al.

(10) Patent No.: US 10,610,690 B2
(45) Date of Patent: Apr. 7, 2020

(54) FULLY IMPLANTABLE TRIAL NEUROSTIMULATION SYSTEM CONFIGURED FOR MINIMALLY-INTRUSIVE IMPLANT/EXPLANT

(71) Applicant: Pacesetter, Inc., Sunnyvale, CA (US)

(72) Inventors: Yelena Nabutovsky, Mountain View, CA (US); Melanie Goodman Keiser, McKinney, TX (US); Gene A. Bornzin, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 401 days.

(21) Appl. No.: 13/940,727

(22) Filed: Jul. 12, 2013

(65) Prior Publication Data

US 2015/0018838 A1 Jan. 15, 2015

(51) Int. Cl.
*A61N 1/375* (2006.01)
*A61N 1/372* (2006.01)
*A61N 1/36* (2006.01)

(52) U.S. Cl.
CPC ......... *A61N 1/375* (2013.01); *A61N 1/36071* (2013.01); *A61N 1/37205* (2013.01); *A61N 1/37241* (2013.01)

(58) Field of Classification Search
CPC ............ A61N 2001/0578; A61N 1/373; A61N 1/37205; A61N 1/3605; A61B 17/34; A61B 1/3468; A61B 1/3417
USPC ......... 606/129, 108, 190, 191; 607/116–119; 600/373–378
See application file for complete search history.

(56) References Cited

U.S. PATENT DOCUMENTS

| 6,847,849 B2 * | 1/2005 | Mamo ................. A61N 1/0551 607/117 |
| 2004/0122477 A1 * | 6/2004 | Whitehurst et al. ............. 607/9 |
| 2004/0215287 A1 * | 10/2004 | Swoyer ............. A61N 1/36071 607/48 |
| 2008/0091255 A1 * | 4/2008 | Caparso ............ A61N 1/36114 607/116 |

(Continued)

FOREIGN PATENT DOCUMENTS

WO    WO 9837926 A1 *    9/1998   .......... A61B 5/0031

*Primary Examiner* — Ryan J. Severson
*Assistant Examiner* — Socrates L Boutsikaris

(57) ABSTRACT

A fully implantable trial neurostimulation system for implant within a patient is provided that includes one or more leads equipped to deliver neurostimulation to patient tissues under the control of a trial neurostimulation control device designed as a capsule for removable implant within the patient. The control capsule is provided with minimal components to power and control the delivery of neurostimulation during a trial evaluation period and is shaped and configured to facilitate removal from the patient following completion of the trial period. In some examples, both the lead and the trial control capsule are removed from the patient following the trial period for replacement with a chronic or long-term neurostimulation system (assuming further neurostimulation is warranted.) In other examples, the lead remains within the patient and the trial control capsule is replaced with a long-term neurostimulation controller device. Various minimally-intrusive implantation procedures are also described.

17 Claims, 7 Drawing Sheets

(56) References Cited

U.S. PATENT DOCUMENTS

| | | | |
|---|---|---|---|
| 2010/0036445 A1* | 2/2010 | Sakai | A61N 1/0551 607/2 |
| 2011/0172679 A1* | 7/2011 | Kuzma | A61N 1/0551 606/129 |
| 2011/0224681 A1* | 9/2011 | McDonald | A61B 17/3401 606/129 |
| 2012/0209285 A1* | 8/2012 | Barker et al. | 606/129 |
| 2012/0215218 A1* | 8/2012 | Lipani | A61B 18/1492 606/41 |

* cited by examiner

FULLY IMPLANTABLE TRIAL NEUROSTIMULATION SYSTEM CONFIGURED FOR MINIMALLY-INTRUSIVE IMPLANT/EXPLANT

FIELD OF THE INVENTION

Aspects of the invention relate to implantable neurostimulation devices such as spinal cord stimulation (SCS) devices and, in particular, to trial SCS systems and methods.

BACKGROUND OF THE INVENTION

SCS is a type of neurostimulation that provides valuable treatment for chronic intractable neuropathic pain, angina pectoris, peripheral vascular disease or other conditions. To this end, an SCS system may be implanted within the body to deliver electrical pulses to nerves along the spinal cord. The SCS system typically includes a generator device similar to a pacemaker but equipped to send electrical pulses to leads mounted along nerves near the spine. The generator is usually implanted in the abdomen or buttock area. The stimulation leads may include thin wires or paddles for delivering electrical pulses to the nerves along the spinal cord. An external controller, similar to a remote control, is provided to allow the patient to control or adjust the neurostimulation.

Currently, prior to permanently implanting an SCS system, the patient undergoes a trial period during which he or she is implanted with a percutaneous lead that is externalized and connected to an external stimulation system. The patient must carry the trial stimulation system with him or her. In United States, patients typically have the trial system for less than a week. In Europe, the trial period can last up to a month. During the trial period, the externalized line can become infected and is very cumbersome for the patient. Therefore, it would be desirable to provide a trial neurostimulation system that is far more comfortable for the patient and substantially impervious to infection, and at least some of the aspects of the invention are directed to these ends.

Note that at least some neurostimulation devices are equipped for both trial operation and subsequent chronic operation. See, for example, U.S. Patent Applications 2006/0190048 and 2006/0195152. With such devices, assuming trial stimulation is successful, the device can be switched from trial mode to chronic mode. If trial stimulation is not successful, the device is explanted. Although such "dual-operation" systems can eliminate the need for a conventional externalized trial system, various issues remain. Since the implantable device must be equipped for full long-term chronic-mode operation (as well as short-term trial operation), it must have all of the components needed for such long-term operation, including a relatively large battery or set of batteries. Accordingly, such dual-operation devices would be at least the same size as chronic neurostimulation devices. There are various burdens and risks associated with initially implanting and subsequently explanting such devices. In particular, if neurostimulation ultimately proves to be unwarranted within a particular patient, that patient must endure the burdens and risks associated with implantation of the full-sized chronic device and then its subsequent explantation.

Accordingly, it would be desirable to instead provide an implantable trial neurostimulation device of relatively small size and smooth shape, which can be easily implanted and subsequently explanted, so as to avoid the burdens associated with trial implantation of a full-size chronic neurostimulation device or dual-operation device. It is to these ends that further aspects of the invention are directed.

SUMMARY OF THE INVENTION

In an exemplary embodiment, a neurostimulation system for implant within a patient is provided that includes: a neurostimulation lead equipped to deliver neurostimulation to patient tissues and a trial neurostimulation device for removable non-chronic implant within the patient. The trial neurostimulation device is equipped to control delivery of neurostimulation using the lead during a trial evaluation period and is configured to facilitate removal from the patient following completion of the trial period. That is, a trial neurostimulation device is provided for temporary (non-chronic) implant within a patient, thereby avoiding the need for an externalized trial device and substantially reducing the risks associated with infection during the trial interval. Since the device is intended only for trial operation, it need not provide all of the components needed for long-term chronic operation such as a relatively large battery. Hence, the device can have a comparatively small size and shape, thus avoiding or reducing the burdens and risks associated with implant and explant of larger devices equipped for chronic operation. Hence, the trial device is designed to be minimally-intrusive during implant and subsequent explant. In some examples, both the lead and the trial neurostimulation device are removed from the patient following the trial period for replacement by a larger chronic neurostimulation system (assuming further neurostimulation is warranted.) In other examples, the lead remains within the patient and the trial neurostimulation device is replaced with a larger chronic neurostimulation controller device.

In an illustrative example, the neurostimulation system is an SCS system having a trial SCS controller device sized and shaped for ease of subcutaneous insertion and removal. For example, the trial device may be in the form of a capsule having a substantially "bullet" shape with smooth and rounded ends to facilitate insertion and removal of the device. A tab or handle may be formed on one end to further facilitate removal of the device following the trial period. If the lead is non-detachably connected to the trial SCS device, the lead is removed along with the capsule following the trial evaluation period for replacement by a chronically-implantable SCS device having one or more of its own leads (assuming the trial stimulation indicates that SCS is warranted.) In other examples, the lead is detachably connected to the capsule via a connector. Following the trial period, the capsule can be disconnected from the lead and removed from the patient while leaving the lead in place. A chronic SCS device is then implanted into the patient and connected to the previously-connected lead for delivery of long-term SCS, The lead may be in the form of any of a variety of otherwise conventional leads, such as percutaneous paddle leads.

In the illustrative example, the capsule includes only the minimal components needed to provide trial SCS. For example, the capsule may include a small printed circuit board (PCB) equipped with minimal control circuitry, a small battery and an antenna for receiving control signals from an external SCS controller. The battery need only provide sufficient power to accommodate delivery of SCS during a trial period of up to thirty days, such as a battery equipped for 400-500 mA-hr of power delivery. Since the trial device is intended for temporary implant only, the capsule need not be biologically hermetic. That is, the capsule does not achieve true hermeticity. In one example, the PCB and any other components of the trial SCS device are simply potted within a suitable epoxy, with the epoxy shaped to form the smooth "bullet" shape. No separate housing or casing is necessarily required.

Preferably, the capsule is sized and shaped to permit insertion into subcutaneous patient tissues using otherwise conventional implantation components and methods (or such components and methods can be modified to accommodate the size of the capsule.) In one particular example, the capsule is sized to fit within a catheter implant sheath. More specifically, in one example, the lead and capsule are implanted by: inserting a guidewire into tissues of the patient using a Tuohy needle (or other suitable tool); inserting an introducer sheath having a dilator; removing the guidewire and the dilator; inserting the lead and the capsule via the sheath; and then removing the sheath to leave the lead and the capsule within the patient. In another example, a splittable Tuohy needle is instead used. Splittable needles are well known in the art. (See, e.g., U.S. Pat. Nos. 4,449,973, 5,322,512 and 5,443,492, each of which is incorporated herein by reference in its entirety. Where a definition or use of a term in a reference, which is incorporated by reference herein is inconsistent or contrary to the definition of that term provided herein, the definition of that term provided herein applies and the definition of that term in the reference does not apply.) A guidewire is inserted into tissues of the patient using the splittable Tuohy needle (where the needle has sufficient width to accommodate insertion of the lead and the capsule.) The lead and the trial device are inserted into patient tissue via the Tuohy needle. The needle is then split open and removed from the patient to leave the lead and the capsule within the patient. In either case, following completion of the trial period, the lead and capsule (or just the capsule) are removed from the patient and replaced with suitable long-term SCS components if further SCS is warranted.

Examples of these and other apparatus, systems and methods are described in detail below.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Figure 1:
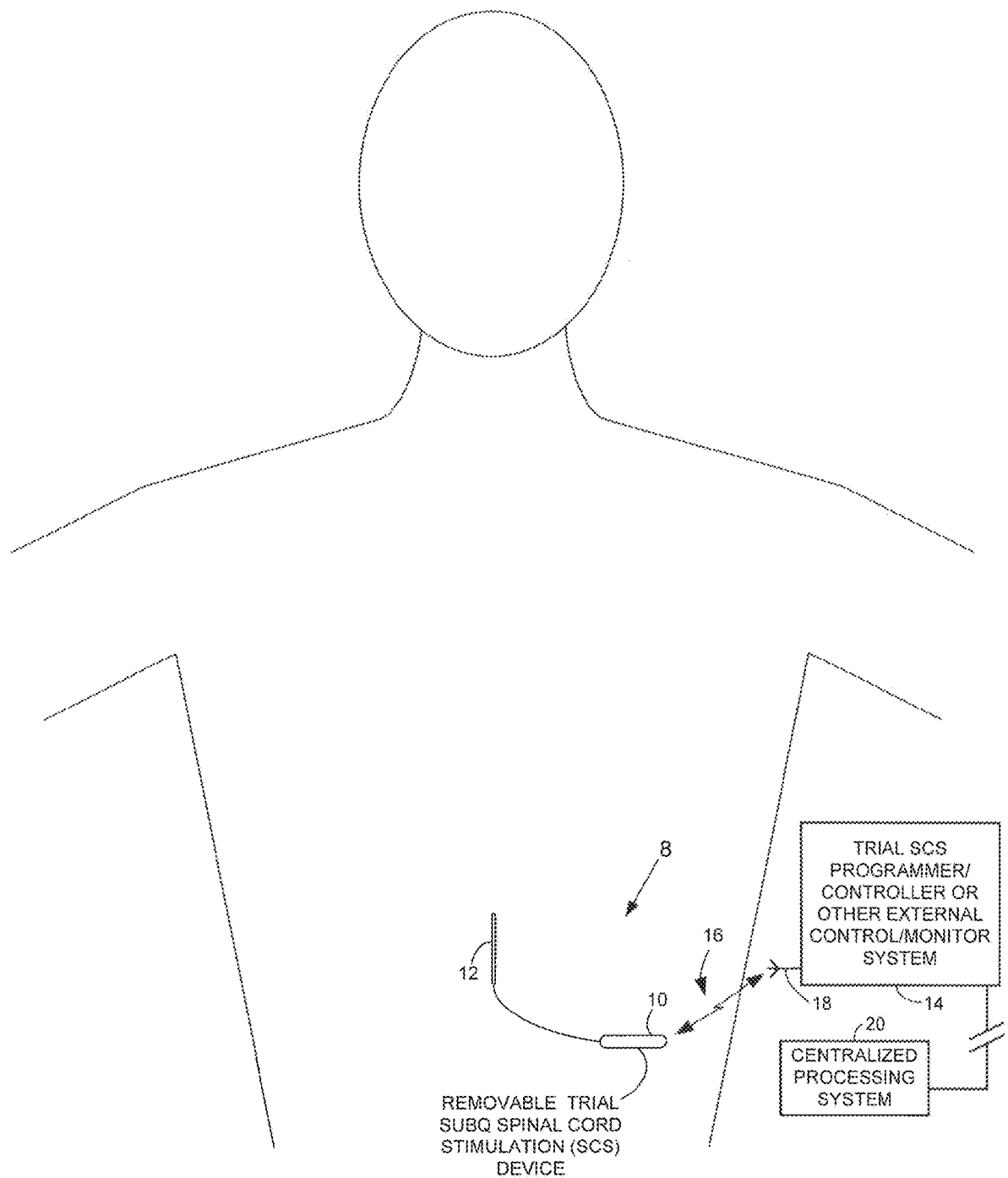
FIG. 1 illustrates pertinent components of a trial neurostimulation system having a small trial SCS capsule device configured for removable implant within a patient.

FIG. 1 illustrates an implantable medical neurostimulation system 8 having a removable acute (i.e. non-chronic) trial subcutaneous (subQ) SCS capsule device 10 equipped to deliver trial SCS or other forms of neurostimulation via one or more leads 12 during a trial SCS evaluation period or interval. Trial SCS capsule 10 and lead 12 are shown in FIG. 1 in stylized form. More detailed illustrations of exemplary trial SCS systems are provided in FIGS. 2 and 3, described below. The lead may be implanted within the epidural space. Trial SCS capsule 10 is equipped to receive control signals from an external SCS programmer/controller 14 (or other external control/monitor system) via a wireless communication link 16 sent from an antenna or other suitable telemetry device 18 (which may include a telemetry wand.) Such control signals may specify combinations of SCS control parameters (such as pulse frequencies, amplitudes, durations, etc.) to allow the efficacy of such parameters to be evaluated by the patient during the trial period. Additionally, the trial SCS capsule can be equipped to transmit signals back to the external system, such as signals confirming receipt of control signals or signals providing diagnostic data pertinent to operational status, battery life, etc. As noted, a telemetry wand may be employed and/or the programmer/controller itself may be hand-held. Typically, the patient will adjust the SCS control parameters in an attempt to identify a combination of parameters sufficient to mitigate pain. If pain is adequately addressed, the SCS trial is deemed successful and the trial capsule is replaced with a full SCS device equipped for chronic or long-term implant.

Data pertaining to the SCS trial can be forwarded to a centralized processing system 20 for convenient access, for example, by the patient's primary care physician or other clinicians. The various external systems may include (or interface with) such systems as the HouseCall™ remote monitoring system, the Merlin@home™ system or the Merlin.Net™ system, all of St. Jude Medical. Although the example of FIG. 1 shows a trial SCS device, additional or alternative trial neurostimulation devices might be used such as devices for trial stimulation of other nerves or organs of the patient.

Figure 2:
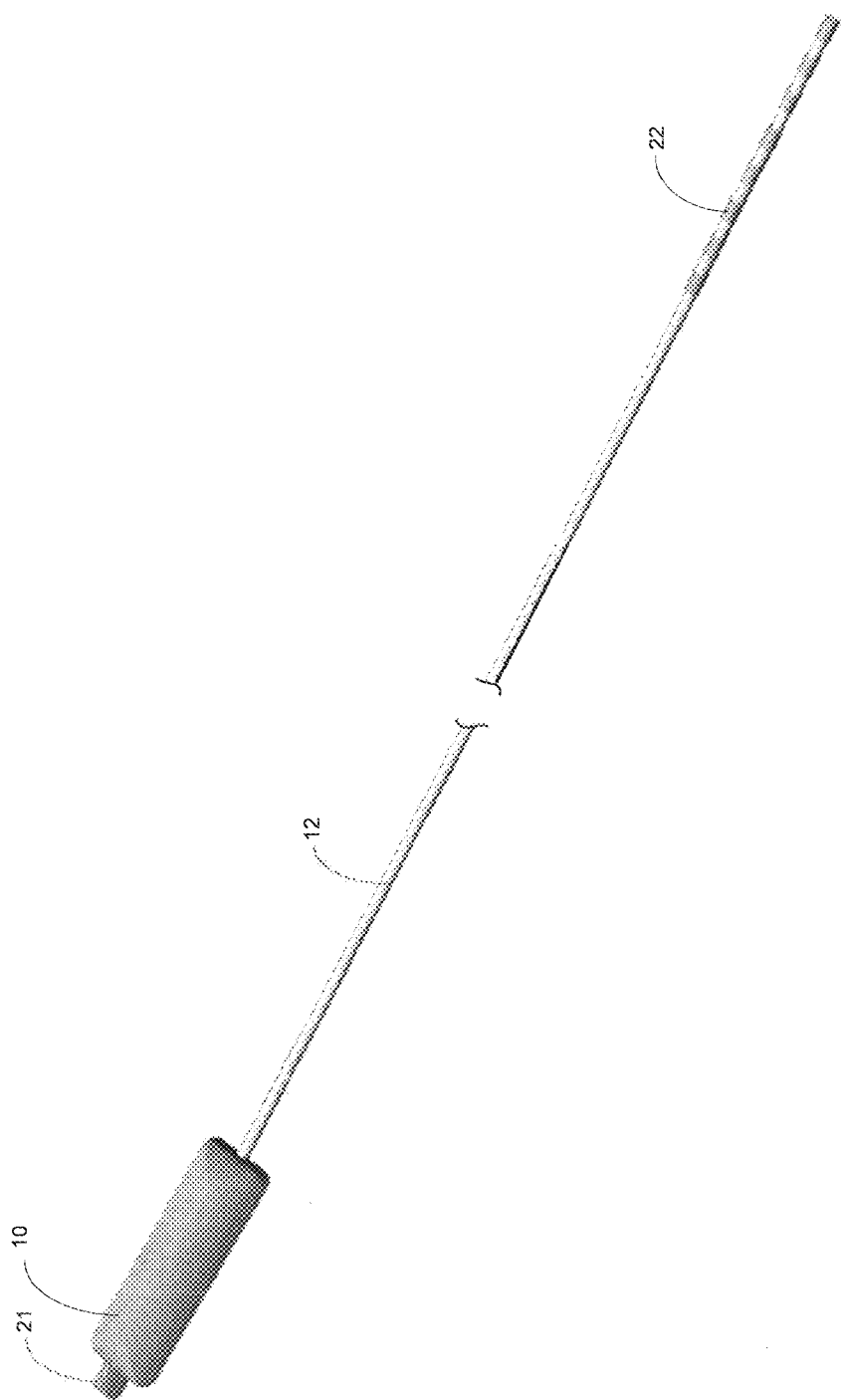
FIG. 2 illustrates an exemplary embodiment of the trial SCS capsule of FIG. II wherein the lead is nondetachably affixed to the trial device.
Figure 3:
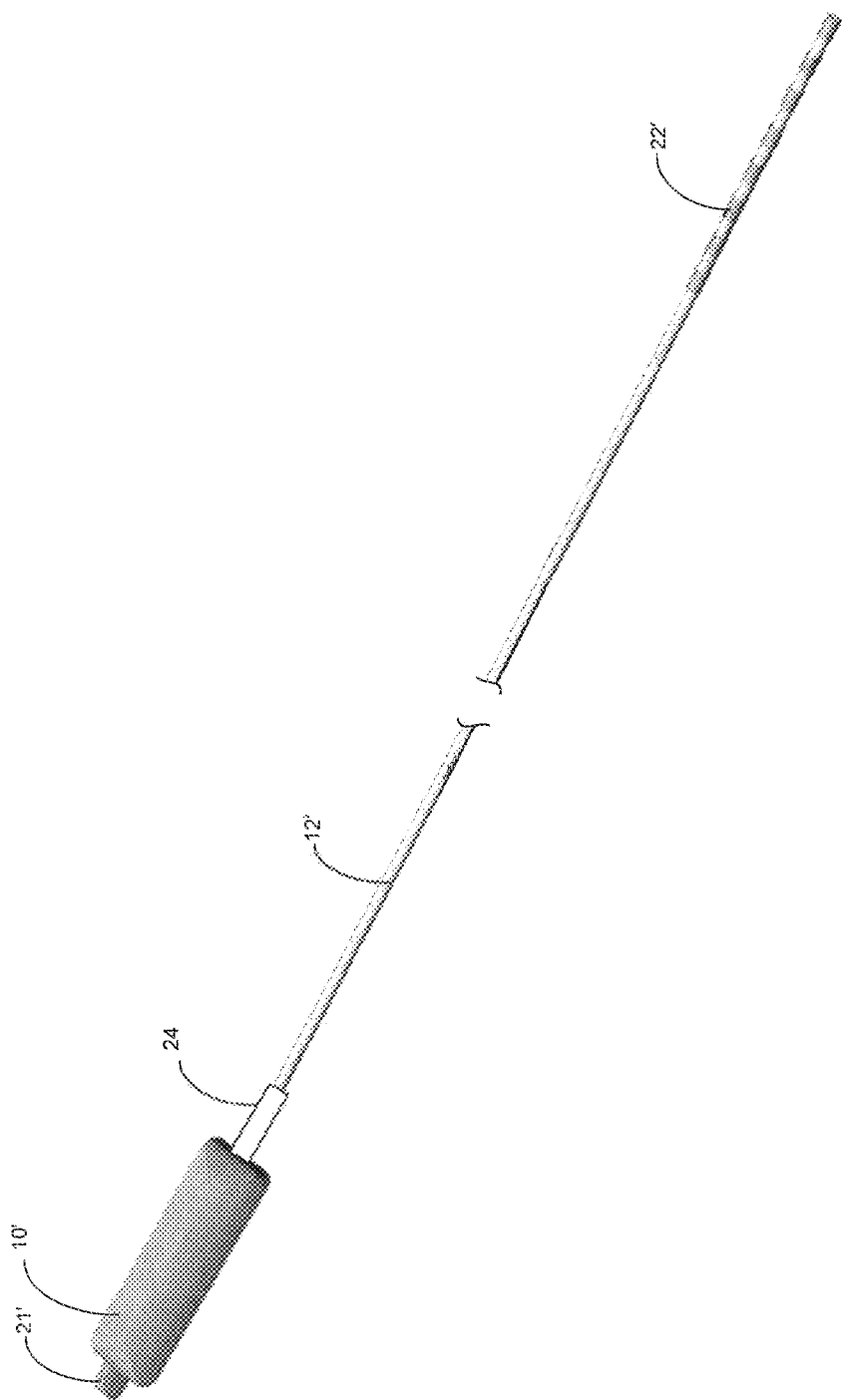
FIG. 3 illustrates an exemplary embodiment of the trial SCS device of FIG. 1 wherein the lead is detachably connected to the trial capsule.

FIG. 2 illustrates an exemplary implementation where trial SCS capsule 10 has a generally or substantially "bullet" shape with smoothed or rounded edges to facilitate insertion and removal. The capsule further includes a tab or handle 21 on its proximal end to facilitate manual removal of the device following the trial period, which can be less than a week or up to thirty days. In the particular example of FIG. 2, lead 12 is non-detachably affixed into the electronics of the capsule and includes a set of eight electrodes 22 (such as provided within the Octrode™ lead, which is a type of linear eight electrode percutaneous lead provided by St Jude Medical.) FIG. 3 illustrates an alternative implementation where lead 12' with electrodes 22' is detachably connected to trial SCS capsule 10' (having removal tab 21') via a suitable electrical connector 24. In both examples, the capsule itself is preferably sized and shaped to permit implant using otherwise conventional implant tools such as guidewires, dilatable sheaths, Tuohy needles, etc. In one example, trial SCS capsule 10 has a length of about 13 to 26 mm, a width of about 7 to 24 mm and a height of about 4 to 8 mm. Of course, if the trail period is around a week or less (as is the requirement in most of the world) the device can be dimensioned to be smaller than in some European countries requiring trial periods on the order of 30 days. Although FIGS. 2 and 3 show only a single lead connected to the trial SCS capsule, additional leads might be accommodated as well.

Figure 4:
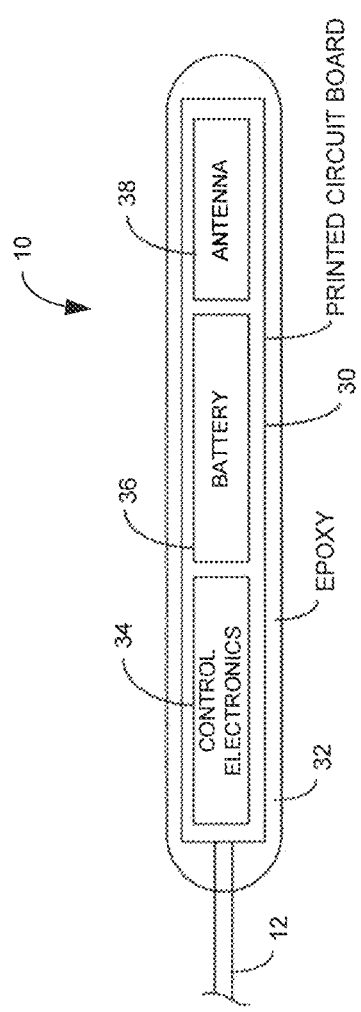
FIG. 4 illustrates exemplary internal components of the trial SCS capsule of FIG. 1, partially in block diagram form.

FIG. 4 illustrates components of an exemplary trial SCS capsule 10, which includes a PCB 30 encased, embedded or potted within an epoxy 32, which is formed or shaped into the smoothed "bullet" shape. The PCB includes control electronics 34, a battery or other power suitable source 36 and an antenna or other suitable wireless communication system 38. The epoxy need not render the device biologically hermetic since it is only intended for temporary (non-chronic) implant of up to thirty days or so. Otherwise conventional techniques can be used to identify and select epoxies suited for non-chronic implant. The battery need only provide adequate power for that relatively brief interval as well. Based on the following exemplary parameters: Pulse width=400 μs; Constant current=10 mA; Electrode impedance=800Ω; Frequency=50 Hz (and assuming stimulation twenty-four hours per day), a 43 mA-hr battery lasts about three days and a 430 mA-hr battery lasts about thirty days. Hence, a battery in the range of 400-500 mA-hr should suffice for even a thirty day trial (and many such trials will be far shorter, often less than one week.)

Figure 5:
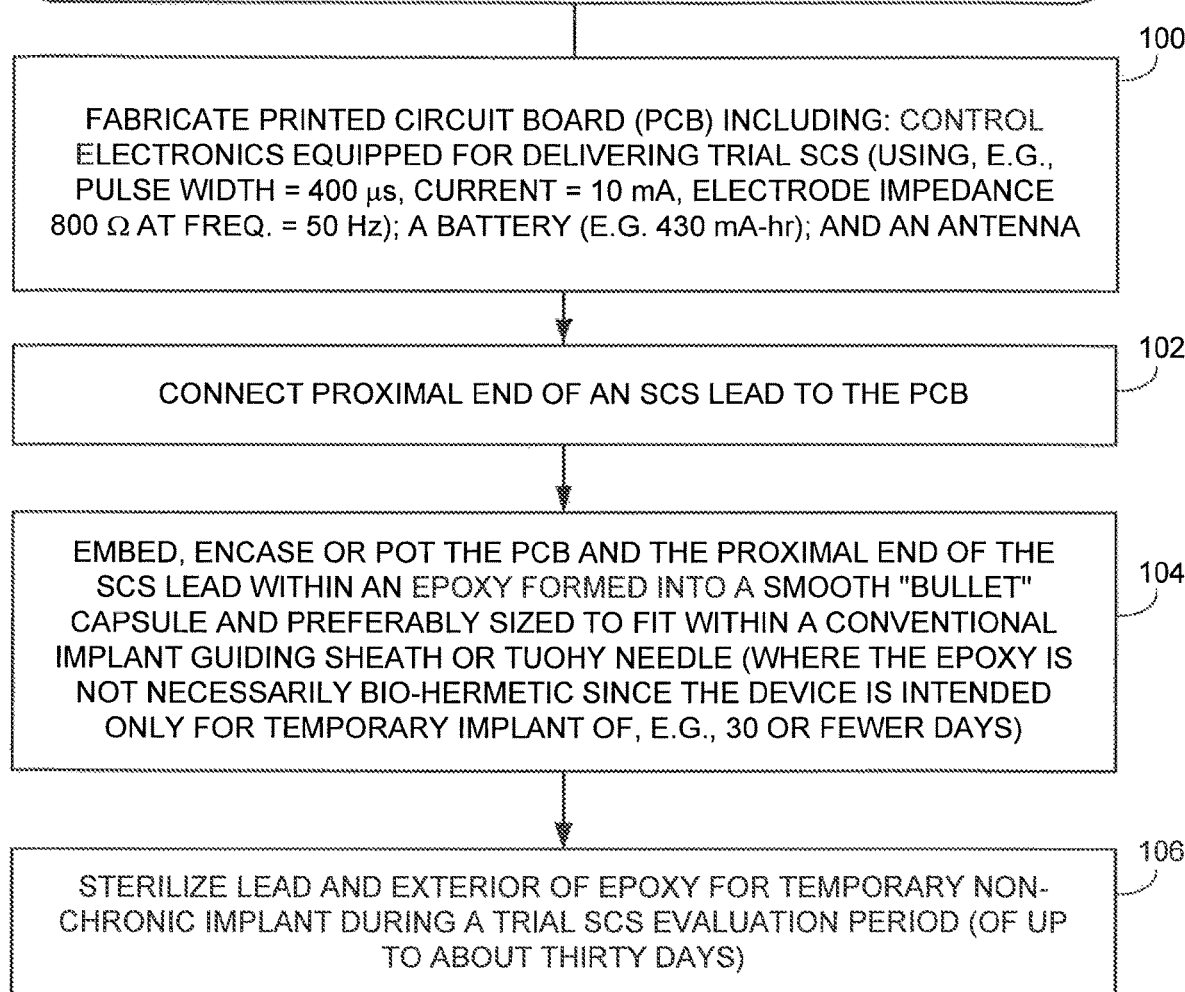
FIG. 5 provides an overview of an exemplary method for designing and fabricating the trial SCS capsule of FIG. 1.

FIG. 5 summarizes exemplary design and fabrication techniques. Briefly, at step 100, a PCB is fabricated including: control electronics equipped for delivering trial SCS (using, e.g., the aforementioned exemplary SCS parameters of pulse width=400 μs, current=10 mA, electrode impedance 800Ω at freq.=50 Hz); a battery (e.g. 430 mA-hr); and an antenna. At step 102, a proximal end of the SCS lead is connected into the electronics of the PCB. At step 104, the PCB and the proximal end of the SCS lead are embedded, encased or potted within an epoxy formed into a smooth "bullet" shape and preferably sized to fit within a conventional implant-guiding sheath or Tuohy needle (where the epoxy is not necessarily bio-hermetic since the device is intended only for temporary implant of, e.g., thirty or fewer days.) At step 106, the lead and an exterior surface of the epoxy capsule are sterilized for temporary implant during the trial (i.e. non-chronic) SCS evaluation period of up to about thirty days.

Figure 6:
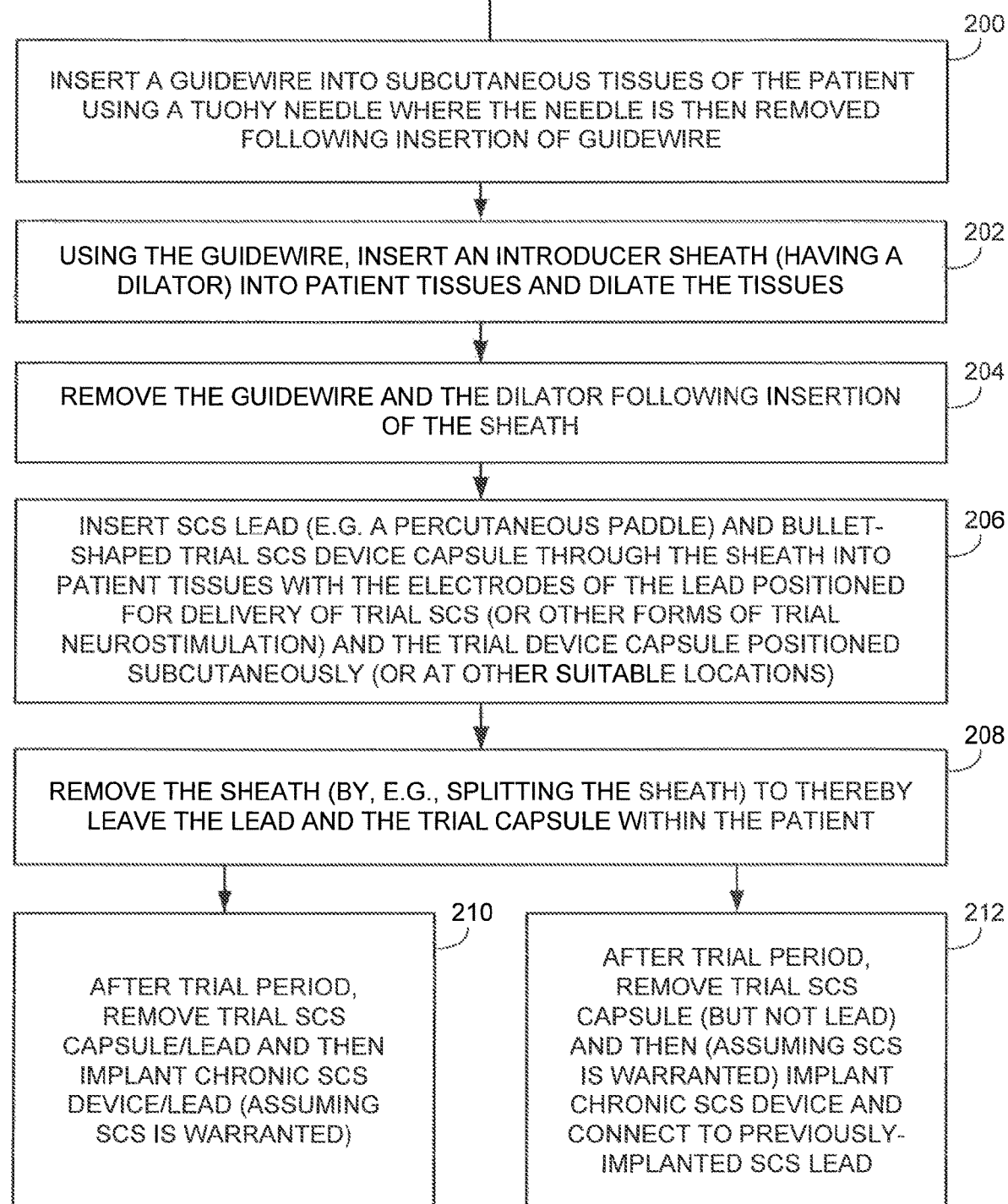
FIG. 6 provides an overview of a first exemplary method for implanting the trial SCS capsule of FIG. 1 wherein a dilatable implantation sheath is employed.

FIG. 6 summarizes a first exemplary implantation technique wherein a dilatable sheath is employed during implant. Briefly, at step 200, a guidewire is inserted by a clinician or surgeon into subcutaneous tissues of the patient using a Tuohy needle where the needle is then removed following insertion of the guidewire. At step 202, using the guidewire, an introducer sheath (having a dilator) is inserted into patient tissues and then the tissues are suitably dilated. At step 204, the guidewire and the dilator are removed following insertion of the sheath. At step 206, an SCS lead (e.g. a percutaneous paddle lead) and a bullet-shaped trial SCS device capsule are inserted through the sheath into patient tissues with the electrodes of the lead positioned for delivery of trial SCS (or other forms of trial neurostimulation) and the trial SCS device positioned subcutaneously (or at other suitable locations within the tissues of the patient.) At step 208, the sheath is removed (by, e.g., splitting the sheath) to thereby leave the lead and the trial SCS capsule within the patient. After the trial period, the system is removed. In this regard, if the lead and trial capsule are not detachable from one another, step 210 is performed wherein both the trial capsule and lead are removed and a chronic long-term SCS device/lead is implanted (assuming SCS is warranted within the patient.) Conversely, if the lead and capsule are detachable from one another, the trial SCS capsule (but not lead) is removed at step 212 and (assuming SCS is warranted) a chronic SCS device is then implanted and connected to the previously-implanted SCS lead.

Figure 7:
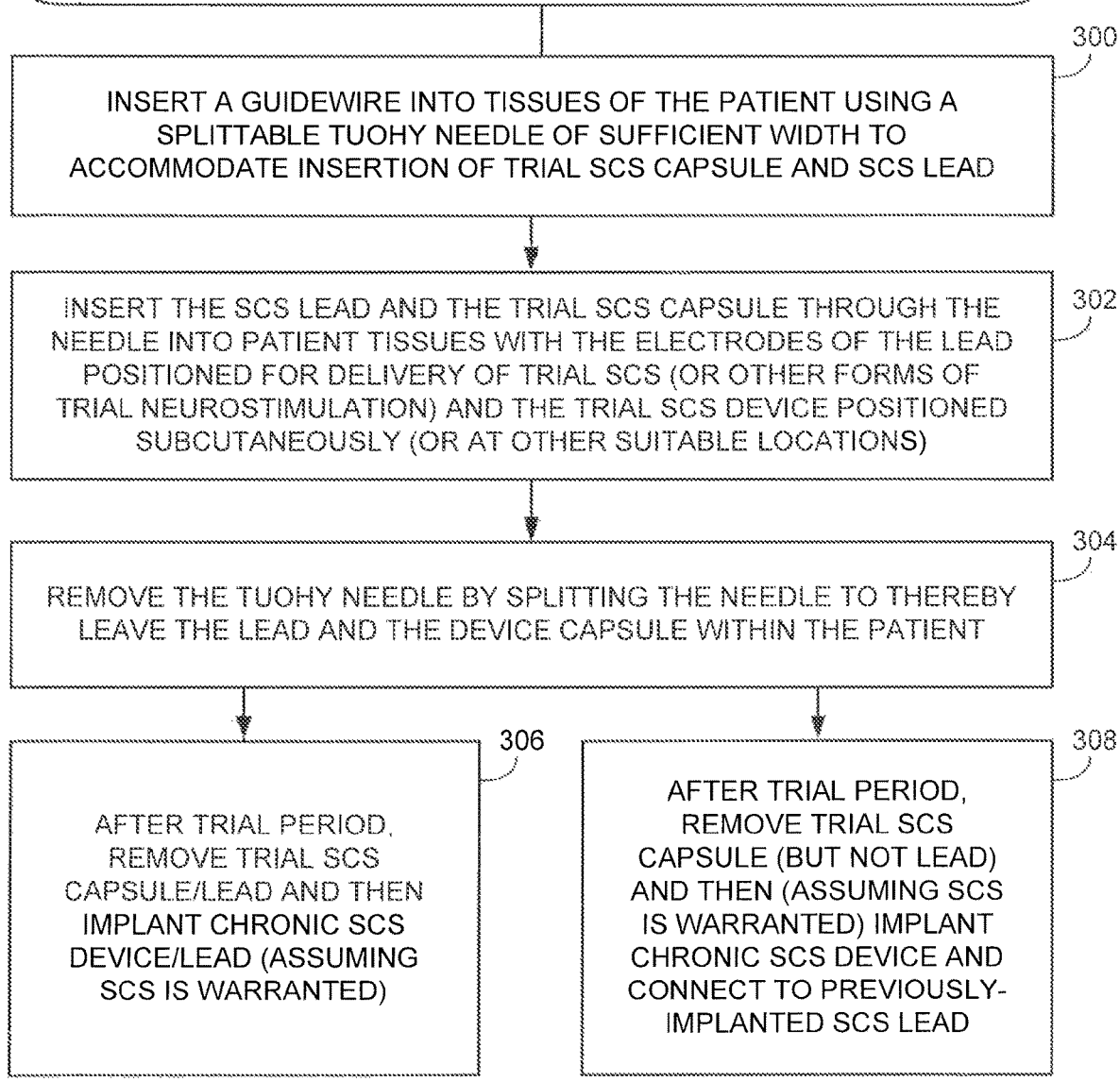
FIG. 7 provides an overview of a second exemplary method for implanting the trial SCS capsule of FIG. 1 wherein a splittable Tuohy needle is employed.

FIG. 7 summarizes a second exemplary implantation technique wherein a splittable Tuohy needle is instead employed. Briefly, at step 300, a guidewire is inserted into tissues of the patient using a splittable Tuohy needle of sufficient width to accommodate insertion of the trial SCS capsule and the SCS lead. At step 302, the SCS lead and the trial SCS capsule are inserted through the needle into patient tissues with the electrodes of the lead positioned for delivery of trial SCS (or other forms of trial neurostimulation) and the trial SCS device is positioned subcutaneously (or at other suitable locations.) At step 304, the Tuohy needle is removed by splitting the needle to thereby leave the lead and the trial SCS capsule implanted within the patient. As in the preceding example, after the trial evaluation period is complete, all or a portion of the system is removed. Again, if the lead and capsule are not detachable from one another, the trial capsule and lead are both removed and a chronic long-term device/lead is implanted (step 306.) If the lead and capsule are detachable from one another, only the trial capsule is removed (step 308) and a chronic SCS device is implanted and connected to the previously-implanted SCS lead.

Thus, a variety of exemplary systems and techniques have been described for use in designing, fabricating and implanting trial neurostimulation systems. Among other advantages, the systems and techniques described herein provide one or more of: a) an SCS trial system that is fully implantable and yet easily removable; b) a SCS trial system that avoids infection; c) an SCS trial system that is much more comfortable for patient than predecessor systems wherein only the lead is implanted and the SCS controller device is kept external to the body; d) an SCS trial system that is low-cost; and e) an SCS trial system of relatively small size and shape (i.e. a small capsule not equipped for chronic SCS) that can be easily implanted and removed.

In general, while the invention has been described with reference to particular embodiments, modifications can be made thereto without departing from the scope of the invention. Note also that the term "including" as used herein is intended to be inclusive. i.e. "including but not limited to."

What is claimed is:

1. A method for implanting a fully implantable spinal cord stimulation (SCS) system within a patient, the system having a SCS lead equipped to deliver SCS to patient tissues and a non-chronic trial SCS device for removable implant within the patient during a trial SCS period, the method comprising:
inserting a guidewire into tissues of the patient; inserting an introducer sheath having a dilator;
removing the guidewire and the dilator wherein the dilator is removed prior to removing the sheath;
inserting the SCS lead and the trial SCS device into the sheath with the SCS lead connected to the trial SCS device, wherein the trial SCS device comprises a capsule, wherein the capsule comprises a battery;
utilizing the sheath to position an electrode of the SCS lead at a SCS delivery position;
utilizing the sheath to position the trial SCS device at a subcutaneous position;

removing the sheath to leave the SCS lead and the trial SCS device within the patient and;

removing at least the trial SCS device following the trial SCS period.

2. The method of claim 1, wherein inserting the guidewire into tissues of the patient comprises inserting the guidewire into subcutaneous tissues of the patient and is performed using a Tuohy needle, and wherein the needle is removed following insertion of the guidewire and prior to inserting the sheath.

3. The method of claim 2, wherein removing the sheath is performed by spitting the sheath.

4. The method of claim 1, further including the step of also removing the SCS lead following the trial SCS period.

5. The method of claim 1, further including the step of implanting a chronic SCS device following the trial SCS period.

6. The method of claim 5, wherein the battery of the trial SCS device is configured to provide power delivery for an interval of between 1 week and 30 days, before removing the trial SCS device and implanting the chronic SCS device following the trial SCS period.

7. The method of claim 1, wherein the SCS lead comprises a plurality of electrodes.

8. The method of claim 1, wherein the SCS lead and the trial SCS device are not encapsulated together and wherein the SCS lead comprises a plurality of electrodes.

9. The method of claim 1, wherein the trial SCS device includes a tab and wherein the method further comprises extracting the trial SCS device from the patient using the tab and replacing the trial SCS device with a larger SCS device.

10. The method of claim 1, wherein inserting the SCS lead and the trial SCS device via the sheath comprises inserting the SCS lead and the trial SCS device via the sheath into subcutaneous tissues, and wherein removing the sheath to leave the SCS lead and the trial SCS device within the patient comprises removing the sheath so that the SCS lead and the trial SCS device are left within the subcutaneous tissues of the patient.

11. The method of claim 1, further comprising dilating the tissues of the patient after inserting the sheath having the dilator.

12. The method of claim 1, wherein the battery is configured for 400 to 500 mA-hr of power delivery.

13. The method of claim 1, wherein the capsule comprises a printed circuit board (PCB), wherein the PCB comprises control electronics configured to deliver trial SCS using a pulse width of 400 ps, a current of 10 mA, an electrode impedance of 800 ohms at a frequency of 50 Hz, and wherein the battery is configured for 430 mA-hr of power delivery.

14. The method of claim 1, wherein the capsule has a length of about 13 to 26 mm, a width of about 7 to 24 mm, and a height of about 4 to 8 mm.

15. The method of claim 1, wherein the battery is configured to provide power delivery for an interval of up to 30 days for the trial SCS period.

16. The method of claim 1, wherein the trial SCS period is no more than 30 days in length.

17. The method of claim 16, further comprising detaching the SCS lead from the trial SCS device prior to removing the trial SCS device, implanting a chronic SCS device and connecting the chronic SCS device to the SCS lead previously implanted when implanting the trial SCS device.

* * * * *